United States Patent
Smith

(10) Patent No.: US 8,608,881 B2
(45) Date of Patent: Dec. 17, 2013

(54) METHOD OF FORMING A BREAST PROSTHESIS

(76) Inventor: Wendy A. Smith, West St. Paul (CA)

( * ) Notice: Subject to any disclaimer, the term of this patent is extended or adjusted under 35 U.S.C. 154(b) by 359 days.

(21) Appl. No.: 13/055,578

(22) PCT Filed: Aug. 5, 2009

(86) PCT No.: PCT/CA2009/001071
§ 371 (c)(1),
(2), (4) Date: Jan. 24, 2011

(87) PCT Pub. No.: WO2010/015075
PCT Pub. Date: Feb. 11, 2010

(65) Prior Publication Data
US 2011/0120616 A1    May 26, 2011

(30) Foreign Application Priority Data
Aug. 6, 2008 (CA) .................................... 2638612

(51) Int. Cl.
*A61F 2/12* (2006.01)
(52) U.S. Cl.
USPC ........................................................ 156/61
(58) Field of Classification Search
USPC ........................................................ 156/61
See application file for complete search history.

(56) References Cited

U.S. PATENT DOCUMENTS

| | | | |
|---|---|---|---|
| 4,401,492 A * | 8/1983 | Pfrommer | 156/61 |
| 6,520,989 B1 | 2/2003 | Eaton | |
| 6,660,304 B2 * | 12/2003 | Nitikhunkasem et al. | 424/489 |
| 7,058,439 B2 | 6/2006 | Eaton et al. | |
| 2003/0014108 A1 | 1/2003 | Lauren | |
| 2004/0176841 A1 * | 9/2004 | Ferguson | 623/7 |
| 2006/0025859 A1 | 2/2006 | Stelter et al. | |
| 2007/0267131 A1 * | 11/2007 | Reitmeter et al. | 156/242 |

FOREIGN PATENT DOCUMENTS

| | | | |
|---|---|---|---|
| DE | 29520574 | | 2/1996 |
| GB | 2121291 A | * | 12/1983 |
| GB | 2284166 | | 5/1995 |
| GB | 2284166 A | * | 5/1996 |
| NL | 9101569 A | * | 4/1993 |
| WO | 03/017868 | | 3/2003 |

* cited by examiner

*Primary Examiner* — Jeff Aftergut
(74) *Attorney, Agent, or Firm* — Ryan W. Dupuis; Kyle R. Satterthwaite; Ade & Company Inc.

(57) ABSTRACT

A breast prosthesis is formed by providing a core of low density foam, shaping the core in the general form of a breast, and applying an outer layer of resilient skin to an outer side of the core to substantially resemble a breast. The inner side of the core opposite the outer side is shaped for mating engagement with a user. A plurality of interchangeable covers of flexible material are each arranged to releasably span the inner side of the core. Typically, coloring is provided on the outer side to resemble an areola of the breast and a protrusion arranged to resemble a nipple of the breast is releasably adhered to the outer side at various positions relative to the areola.

19 Claims, 5 Drawing Sheets

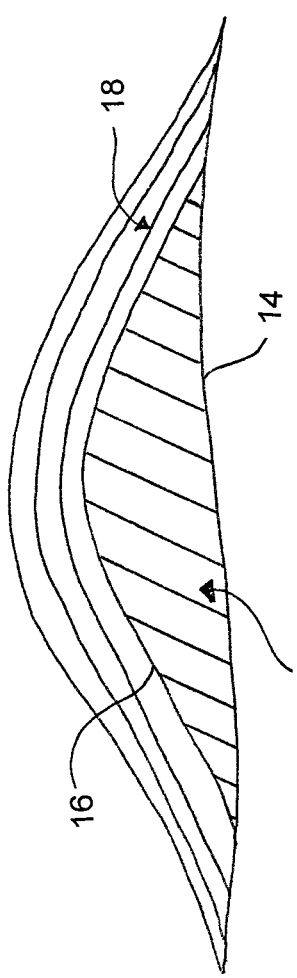
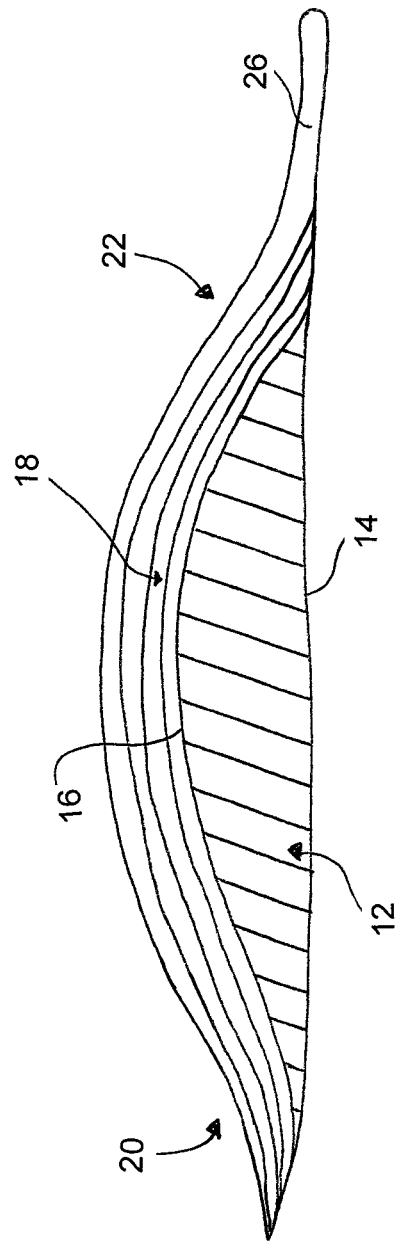

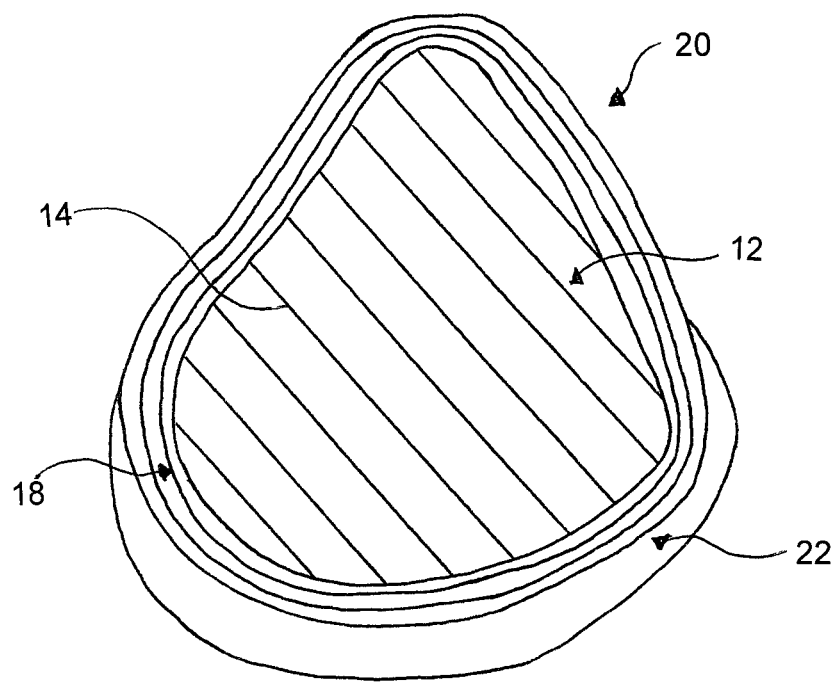
FIG. 6
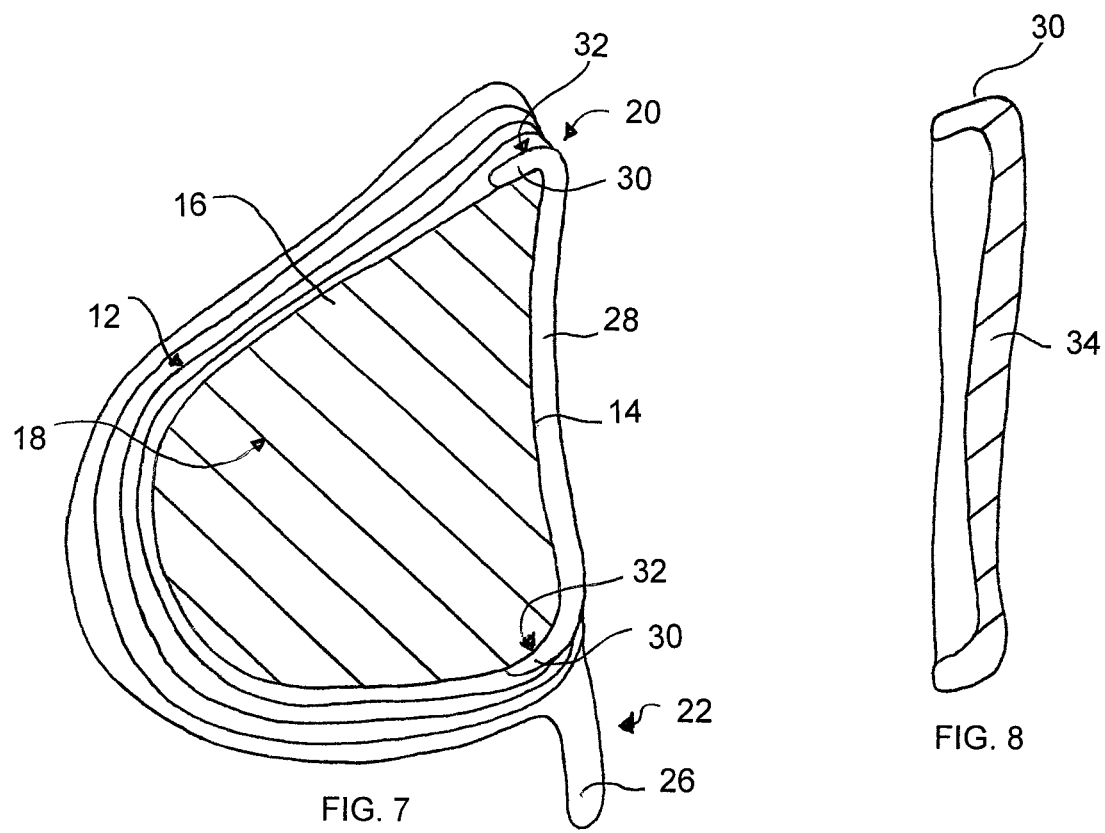
FIG. 7
FIG. 8

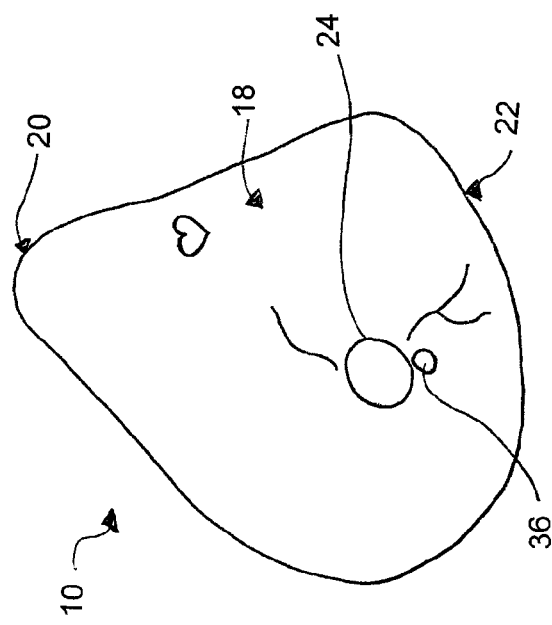
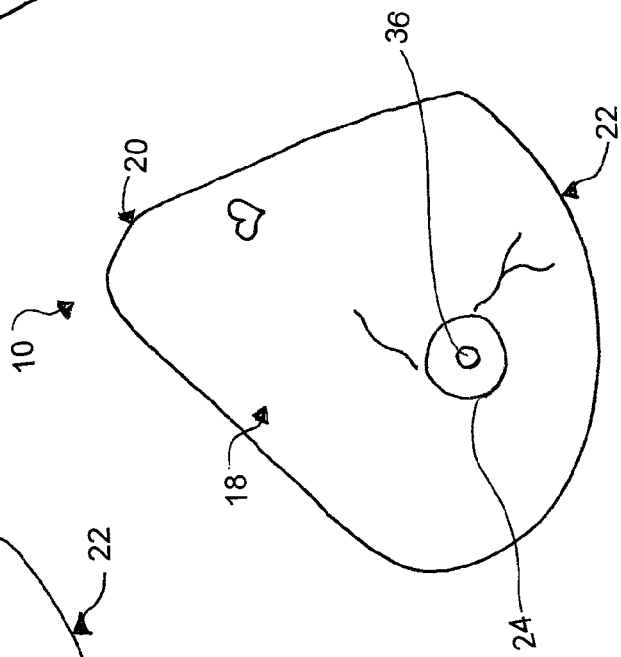
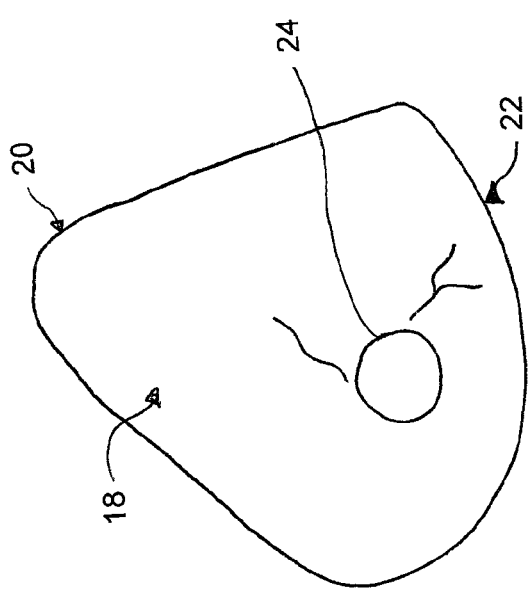

METHOD OF FORMING A BREAST PROSTHESIS

This application claims priority benefits from Canadian Patent Application 2,638,612 filed Aug. 6, 2008.

FIELD OF THE INVENTION

The present invention relates to a breast prosthesis to be worn externally by a user and a method of forming the prosthesis.

BACKGROUND

A common form of breast prosthesis is worn externally to avoid unnecessary surgery. A common example of a breast prosthesis is disclosed in Canadian application 2,105,348 by Schulz et al. The prosthesis is formed by a flexible skin which defines the exterior shape of the prosthesis and which encapsulates a flowable gel therein. By defining the shape of the prosthesis solely by a thin exterior skin, only a limited number of sizes are available so that the prosthesis is ill suited to many users. Furthermore the resulting structure is very heavy and causes many problems to the user due to the shifting mass during various activities performed by the user. The construction is also susceptible to damage by puncturing the outer skin such that the prosthesis cannot be repaired and is no longer of use. Other problems associated with a prosthesis of this type include a fixed nipple location as the nipple location on the prosthesis will not react to different garment types in the same manner as a natural breast. Further problems arise due to the flexible skin required to encapsulate the rear side of the prosthesis which is worn against the skin of the wearer as the skin is not well-suited to accommodate different preferences of different users for comfort.

SUMMARY OF THE INVENTION

According to one aspect of the invention there is provided a method of forming a breast prosthesis comprising:

providing a core formed of low density foam material;

shaping a first side of the core to be substantially dome shaped so as to be substantially in a form of a breast; and applying an outer layer of resilient skin to the first side of the core.

By providing a foam core to which outer layers are then applied to form the resilient skin, the outer layer can be formed very thin, for example by spraying on, so as to minimize use of dense materials in forming the prosthesis, thus resulting in a very light weight prosthesis which is more comfortable for the user. Furthermore the outer layer of resilient skin can be applied to the foam core in an uncured state so that the curing of the outer layer onto the core is sufficient for readily bonding the different materials of the prosthesis together. The construction of the present invention can also be readily repaired in the event of any damage unlike prior art configurations which may potentially leak.

The method preferably includes shaping the first side of the core to be substantially dome shaped before applying the outer layer of resilient skin to the first side of the core.

The resilient skin may be formed to comprise silicone arranged to retain shape in a cured form.

The outer layer or resilient skin is preferably applied such that the outer layer has thickness which is less than 20% of an overall thickness of the prosthesis at a central location thereof, and more particular which is near 10% of an overall thickness of the prosthesis at a central location thereof.

Preferably the second side of the core opposite the first side is shaped to mate with a wearer of the prosthesis either before or after the outer layer is applied to the first side.

When a plurality of outer layers of resilient skin are applied to the first side of the core, preferably at least an outermost one of the outer layers is substantially translucent with color being applied between at least some of the outer layers of resilient skin to define at least one of veins, an areola, freckles or a tattoo.

The method may further comprise adhering a nipple protrusion to the outer layer such that the nipple protrusion can be readily detached and reattached to the outer layer at any one of a plurality of mounting locations thereon.

When a representation of an areola is provided on the outer layer of resilient skin, the nipple protrusion is preferably supported to be readily separable from the outer layer and the representation of the areola thereon.

The method may also include providing a cover of flexible material arranged to span a second side of the core opposite the first side, and supporting the cover on the core to span the second side such that the cover is readily separable from the core and the outer layer.

There may be provided a plurality of covers, each formed of a different flexible material and being arranged to span the second side of the core so as to be readily separable from the core in which the plurality of covers are interchangeable with one another.

Preferably a peripheral retaining edge is provided about a perimeter of the second side of the core and retaining a perimeter edge of the cover in relation to the retaining edge about a full perimeter of the cover.

A recessed central portion in the second side of the core which is bound by the peripheral retaining edge preferably mounts the cover therein to be substantially flush with a peripheral edge of the outer layer of resilient skin at the second side of the core.

A resilient bonding layer may be applied to the second side of the core and to an inner side of the cover to retain the cover spanning the second side of the core. A resilient bonding layer may also be applied to an outer side of the cover to retain the cover against a user.

The outer layer of resilient skin may overlap over the second side of the core about a peripheral edge of the core such that the outer layer of resilient skin and the cover are substantially flush with one another at the second side of the core.

A top edge of the core and the outer layer of resilient skin thereon may be shaped to be gradually reduced in thickness towards the peripheral edge thereof.

Along an opposing bottom edge of the core, there may be provided a retainer flange which is arranged to be overlapped by a bra strap of a wearer of the prosthesis. The retainer flange is preferably formed integrally with the outer layer of resilient skin.

The core is preferably formed of a highly flexible and highly resilient low density polyurethane foam material.

According to another aspect of the present invention there is provided a method of forming a breast prosthesis comprising:

providing a core having a first side which is substantially dome shaped;

applying an outer layer of resilient skin to the first side of the core;

shaping a second side of the core opposite the first side for mating engagement with a user of the prosthesis;

providing a cover of flexible material arranged to span the second side of the core; and supporting the cover on the core to span the second side thereof such that the cover is readily separable from the core and the outer layer.

By further providing a cover of flexible material arranged to span the second side of the core, and which is readily removable, the material forming the core can be readily accessed at the second side thereof for ease of trimming for refitting purposes, for example due to weight loss and the like. Furthermore the removable cover readily permits different configurations of covers to be interchanged with one another on the prosthesis according to the different comfort preferences of the users.

According to a further aspect of the present invention there is provided a method of forming a breast prosthesis comprising:

providing a body having a first side which is substantially dome shaped so as to resemble a breast and a second side opposite the first side which is shaped so as to mate with a user of the prosthesis;

providing colouring on the first side of the body arranged to resemble an areola of the breast;

providing a protrusion arranged to resemble a nipple of the breast; and adhering the nipple to the first side of the body so as to be readily separable from the first side of the body.

By further providing a nipple protrusion which can be readily separated and reattached at various locations on the prosthesis, the nipple protrusion can always be located to best match a corresponding natural breast regardless of the type of garment to be worn. By further providing an areola which is fixed relative to the outer skin and which the nipple protrusion is moveable relative thereto, a more realistic areola can be provided in the form of coloring between translucent layers of the resilient skin while the configuration of the nipple protrusion which is readily separable can be simplified in its construction as compared to prior art arrangements.

According to yet another aspect of the present invention there is provided a breast prosthesis comprising:

a core formed of low density foam material comprising a first side substantially dome shaped so as to be substantially in a form of a breast and an opposing second side arranged to be worn against a user; and an outer layer of resilient skin applied to the first side of the core.

Some embodiments of the invention will now be described in conjunction with the accompanying drawings in which:

BRIEF DESCRIPTION OF THE DRAWINGS

FIG. 4 is a sectional view of the prosthesis after initial three outer layers of resilient skin have been applied.

FIG. 5 is a sectional view of the prosthesis after three outer layers of resilient skin and a final translucent outer layer of resilient skin have been applied to the core.

FIG. 6 is a rear elevational view of the second side of the core illustrating the peripheral edges of the outer layers of resilient skin overlapping the first side of the core.

FIG. 7 is a sectional elevational view of the prosthesis with the cover shown spanning the second side of the core opposite the first side supporting the outer layers of resilient skin thereon.

FIG. 8 is a sectional side elevational view of the cover.

FIG. 9 is a front plan view of the outer layers of resilient skin applied to the first side of the core of the prosthesis with the nipple protrusion shown removed.

FIG. 10 is a front elevational view of the prosthesis showing the nipple protrusion supported on the outer layer of resilient skin in alignment with the areola representation.

FIG. 11 is a front elevational view of the prosthesis in which the nipple protrusion is shown supported on the outer layer of resilient skin misaligned with the areola representation.

In the drawings like characters of reference indicate corresponding parts in the different figures.

DETAILED DESCRIPTION

Figure 3:
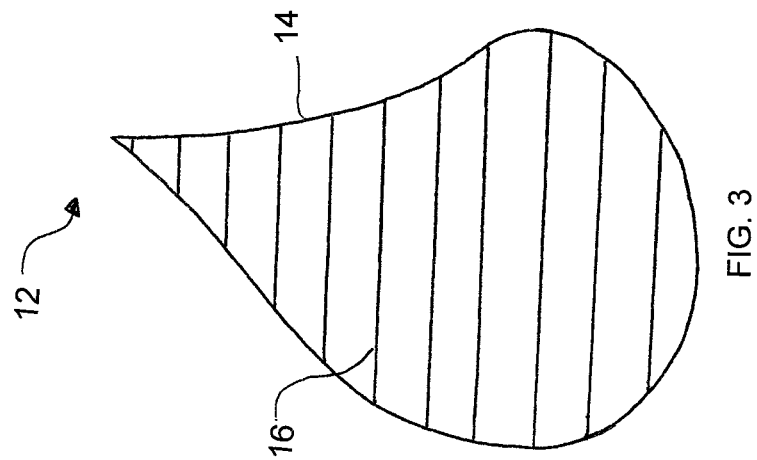
FIG. 2 and FIG. 3 are respective front and side views of the core after shaping to be dome shaped substantially in the form of a breast.
Figure 2:
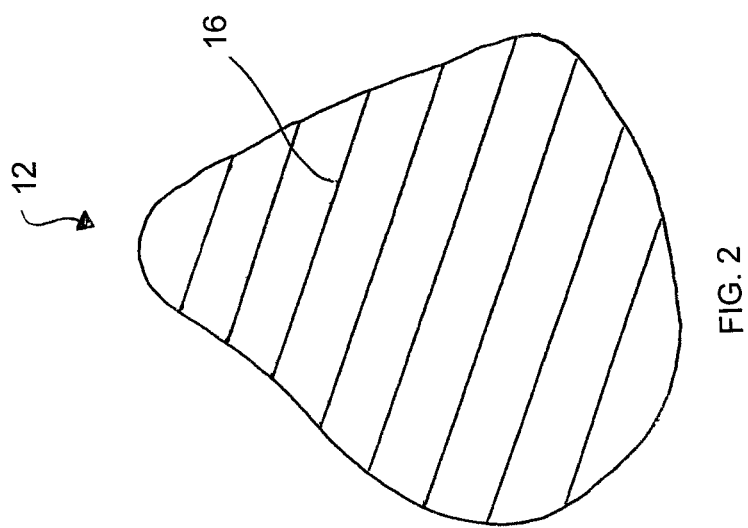

Referring to the accompanying figures there is illustrated a breast prosthesis generally indicated by reference numeral 10. The prosthesis 10 can be readily customized to a particular user, or can have some components manufactured in large numbers for some degree of customization by distributors or the end users.

Although various embodiments are described in the following, the common features of the various embodiments will first be described.

The prosthesis generally comprises an inner core having first inner side 14 to be fitted against the user or wearer of the prosthesis and a second outer side 16 which is substantially dome shaped so as to resemble a breast, and an outer layer 18 of resilient skin which covers the outer side of the core to enhance the resemblance of a natural breast.

More particularly the inner core 12 comprises a closed cell foam having a high degree of resilience and a high degree of flexibility, for example a low density polyurethane foam material. The inner side of the core 12 is shaped and fitted either before or after the outer layers of resilient skin are applied to the outer side of the core. More particularly the inner side 14 is shaped to mate with the corresponding location on the body of the wearer.

The outer side 16 which is shaped to be generally dome shaped is gradually reduced in thickness towards the outer peripheral edge thereof from a central location where the prosthesis is thickest between the inner and outer sides thereof to a surrounding peripheral edge where the prosthesis is at its narrowest. The thickness of the core 12 tapers more gradually from the central location to a top edge 20 than towards an opposing bottom edge 22 which is arranged to be substantially cupped in shape to resemble a natural breast.

The outer layer 18 comprises a silicone which is applied in a plurality of individual layers, which are sequentially applied in an uncured state and cured between applications of the layers so that a single integral layer is formed. When cured, the outer layer 18 is much denser than the core and less flexible than the core so as to retain the shape thereof in a resilient manner.

The overall outer layer 18 formed by individually applied layers is relatively thin as compared to the thickness of the core between the inner and outer sides thereof so as to be typically less than 20% of the overall thickness of the prosthesis at the central portion thereof. Although the prosthesis as illustrated in the figures is not to scale to better emphasize the individually applied layers of the outer layer 18, the outer layer is typically near 10% of the overall thickness of the prosthesis near the central portion so as to be near 50% of the overall weight of the prosthesis or less in mass.

The outer layer 18 is readily adhered to the core simply by application in an uncured state whereby the curing of the outer layer 18 is sufficient for bonding and adhering to the core. The individually applied layers forming the outer layer 18 are generally translucent towards the outermost ones of the layers with the final outermost layer typically being substantially clear. Color is applied between the layers of silicone as well as various details including coloring representing the areola, veins, freckles, and/or a tattoo on the resilient skin of the prosthesis. The resulting areola representation 24 is fixed in location on the outer layer of resilient skin of the prosthesis.

The outer layer 18 is similarly formed to be reduced in thickness towards the peripheral edge of the prosthesis. As best shown in FIGS. 4 and 5, the individually applied layers forming the outer layer 18 are overlapped with one another so as to be reduced to a minimal overall thickness at the outer peripheral edge of the prosthesis. The resulting finished prosthesis follows the general shape of the outer side 16 of the core to be gradually reduced in thickness towards the top edge thereof as well as to the sides.

A retainer flange 26 is formed along the bottom edge of the core 12 to protrude generally radially outward from the central portion of the prosthesis. The retainer flange 26 integrally formed with the outer layers 18 of resilient skin from the same silicone material to form a thin flat clear member of suitable dimensions to be overlapped by the strap of a bra which surrounds the torso of the wearer, for example in alignment with the under wires of a bra having under wires therein.

A cover 28 is provided for spanning the second inner side of the inner core 12 when worn by a user. The cover 28 comprises a thin member of flexible material arranged to match the profile of the inner side of the core when pressed against the body of the wearer.

As shown in FIG. 8, an auxiliary cover is provided of like configuration to the cover 28 in which the auxiliary cover 34 is interchangeable with the cover 28 depending upon the comfort preferences of the wearer. A plurality of auxiliary covers are typically provided in which each is identical in configuration to the cover 28 with the exception of each of the covers being different in material. For example some covers may be formed of silicone or like materials to be water resistant whereas other covers may be formed of a breathable cloth material which is more comfortable for some users. In yet further arrangements the cover may be formed of any material which is suitable for receiving an adhesive thereon for securing the prosthesis against the skin of a wearer.

The prosthesis further comprises a nipple protrusion 36 formed of similar material as the outer layers of resilient skin. The nipple protrusion 36 is arranged to be adhered to the outer layer of resilient skin readily at any one of a plurality of locations depending upon the type of garment worn by the user and the desired appearance of the prosthesis under the garment. The nipple protrusion 36 is thus moveable relative to the areola representation 24 fixed on the outer layer of the prosthesis so that in some instances the nipple protrusion may be aligned with the areola representation as shown in FIG. 10, whereas in other instances the nipple protrusion can be supported misaligned with the areola representation depending upon the desired appearance of the prosthesis under a garment to be worn by the user.

Figure 1:
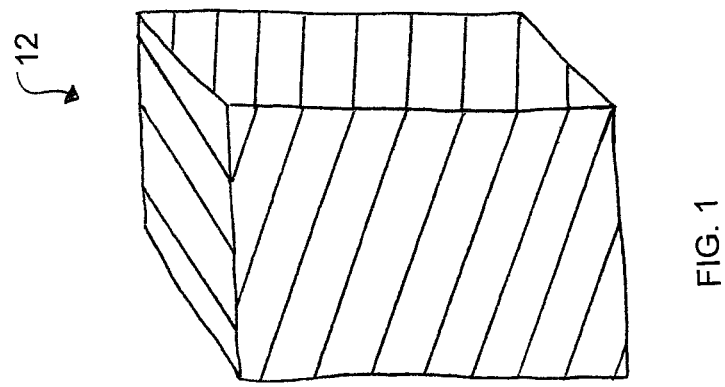
FIG. 1 is a perspective view of an initial block of foam from which the core of the prosthesis is arranged to be formed.

In use, a block of resilient foam as shown in FIG. 1 is initially shaped to form both the inner and outer sides thereof for mating with the body of the patient and for matching the contour of a corresponding natural breast respectively. The outer side is formed before the outer layers of resilient skin are applied thereto, however the inner side of the core may be formed before or after the outer layers are applied to the outer side of the core.

The outer layer is formed by applying silicone in individual layers in an uncured form, for example by painting on the silicone, spraying on the silicone, pasting the silicone onto the core, or molding the silicone directly onto the core. The curing process of the silicone once applied is sufficient for bonding purposes to the foam core.

The individually applied layers forming the outer layer are applied in thin layers which are substantially translucent and which are individually cured. Layers of coloring material are provided between the individually applied layers forming the outer layer. Color is applied to represent skin coloring, freckles, veins, and an areola representation 24. A tattoo representation can also be applied between some of the individually applied layers forming the outer layer 18. Typically at least one outermost final coat is provided on the outer layer 18 which is clear for a more realistic appearance and for integrally forming the retainer flange along the bottom side thereof.

When the silicone is cured, it substantially retains its shape while being sufficiently flexible to have a realistic appearance. A material for the cover is selected based upon user preferences and then the peripheral edge thereof is inserted into a suitable retaining groove to support the cover spanning the inner rear side of the core. Even once supported on the core, the cover remains readily separable for interchanging the cover with auxiliary covers of similar configuration but formed of different material.

Finally a nipple is attached by suitable adhesive to the outer layer of resilient skin so as to remain readily separable and ready to be reattached at any one of plural different locations thereon.

In the event that the prosthesis needs to be refitted to the wearer, due to weight loss and the like, the cover can be readily removed so that the foam material of the core can be readily accessed at the inner side thereof for trimming as may be required.

Once the prosthesis has been assembled, the prosthesis is readily worn by mating the rear inner side of the prosthesis to the body of the wearer in position such that when a bra is worn, the strap of the bra extending about the torso below the cups of the bra is arranged to overlap the retainer flange 26 of the prosthesis to further retain the prosthesis in position.

Turning to the first embodiment, best shown in FIG. 7 a perimeter flange 30 is provided about the full periphery of the cover 28 which is arranged to be received within a corresponding peripheral groove 32 formed about the periphery of the core 12 between the material of the core 12 and the material of the outer layers 18 of resilient skin. The edge flange 30 of the cover is arranged to be more rigid than the central main portion of the cover to ease insertion of the edge flange 30 into the peripheral groove 32 at the rear inner side of the prosthesis. After the outer layers of silicone are cured, the peripheral groove 32 is formed by separating a peripheral edge portion of the outer layer 18 from the core about a full periphery thereof. The peripheral edge of the cover comprises a generally annular band which projects generally perpendicularly from the central portion of the cover to the free edge thereof so as to be suitable oriented for insertion into the peripheral groove.

Figure 12:
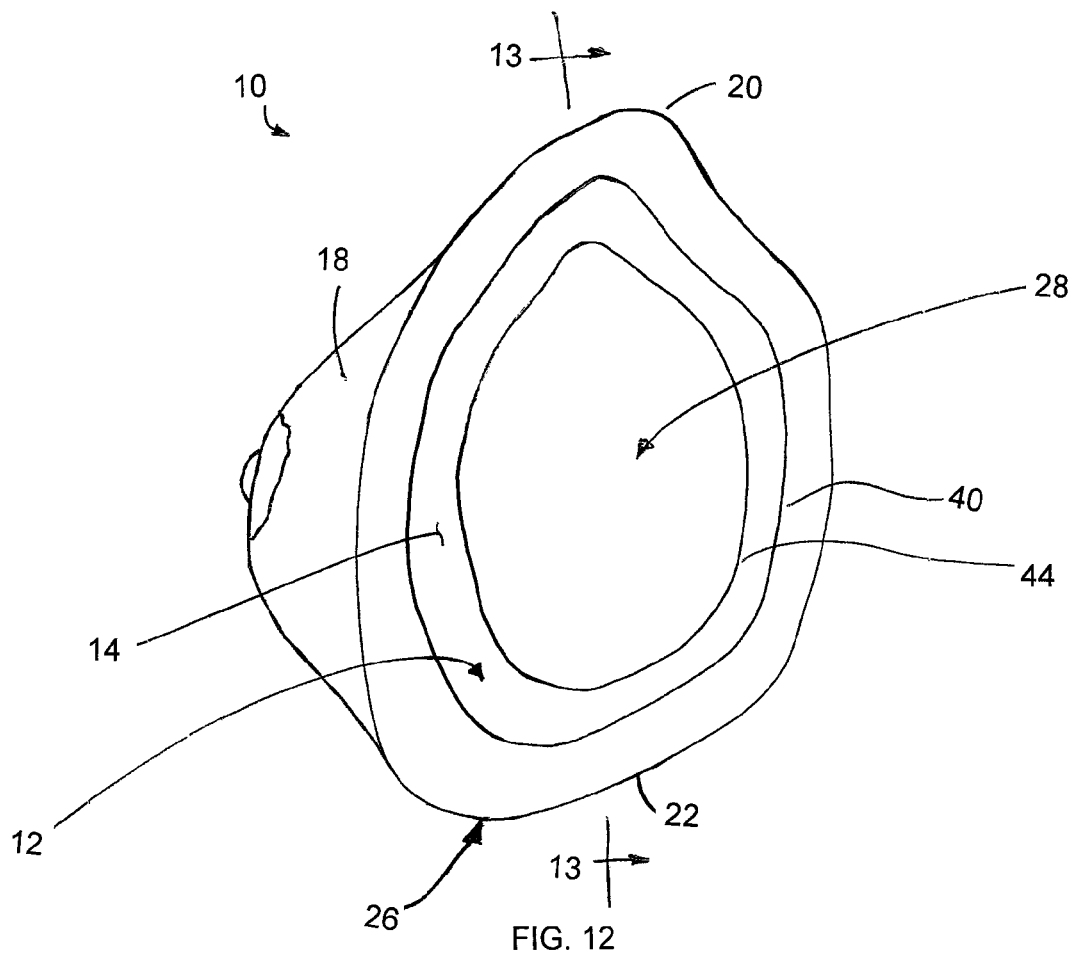
FIG. 12 is a perspective view of a rear inner side of a further embodiment of the prosthesis.
Figure 13:
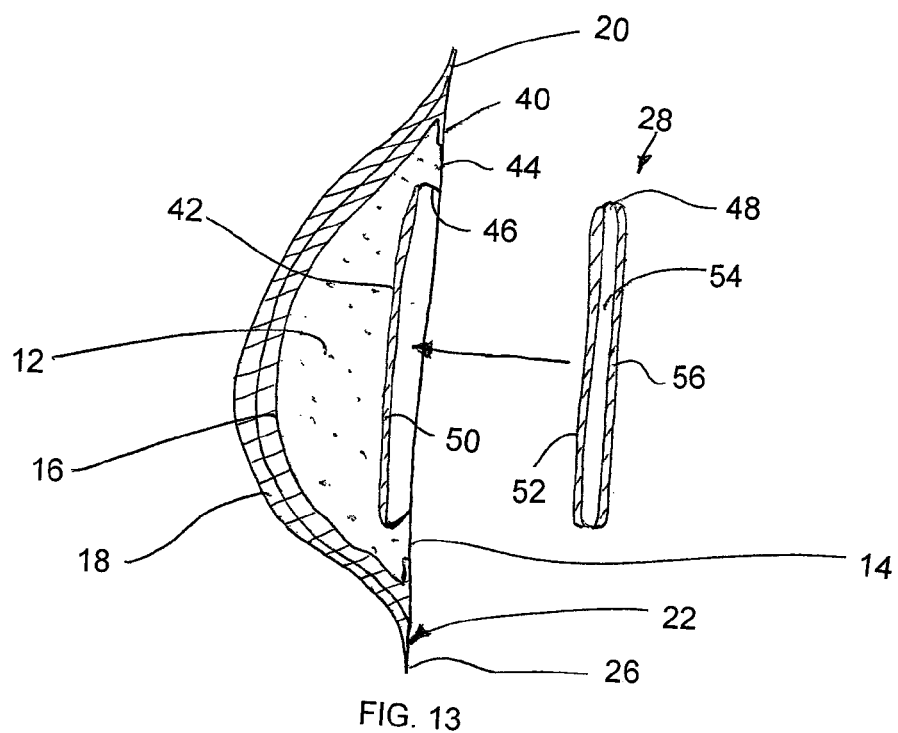
FIG. 13 is a sectional view along the line 13-13 of FIG. 12.

Turning now to FIGS. 12 and 13 there is illustrated a further embodiment of the prosthesis 10. In this instance the prosthesis 10 is substantially identical to the previous embodiment with regard to the steps of providing an inner core 12 of foam material having first inner side 14 for conforming to the wearer and a second outer side 16 which is substantially dome shaped to resemble a breast. The outer layer of resilient skin 18 is applied in a manner similar to what is described above with regard to the previous embodiment in that silicone is applied in layers to the second outer side 16 of the inner core with the outer skin extending outwardly beyond the inner core about a full circumference thereof to define a surrounding flange portion which defines the top and bottom edges 20 and 22 as well as the retainer flange 26. A cover 28 is also provided to span the second inner side 16 similar to the previous embodiment, however the configuration of the cover differs.

The embodiment of FIGS. 12 and 13 is distinguished from the previous embodiment by forming the outer layer of resilient skin to overlap a portion of the inner side 14 only at an outer peripheral portion thereof about a full perimeter so as to define a flange portion 40 of the outer layer 18 which surrounds the circumference of the core 12 to overlap the core from the second outer side 16 to the first inner side 14. The flange portion of the outer layer 18 which spans the inner side at the outer peripheral portion thereof is integral with the main portion of the outer layer which spans the outer side 16 in the manner described above with regard to the previous embodiment.

The inner side 14 of the inner core 12 also differs from the previous embodiment in that there is provided a central recessed portion 42 in which the surface of the inner core at the inner side 14 is recessed in relation to the surrounding perimeter portion 44 which is partially overlapped by the flange portion 40 of the outer layer of resilient skin 18. A peripheral retainer edge 46 is defined about the full perimeter of the central recessed portion 42 in which the surface at the inner side of the core is stepped inwardly from the perimeter portion 44 to the recessed central portion 42.

The retainer edge 46 narrows in cross sectional dimension outward from the inner end adjacent the central portion 42 to the mouth formed by the perimeter portion 44 so that the retainer edge 46 is arranged to overlap the perimeter edge 48 of the cover 28 about a full perimeter thereof to effectively retain the cover 28 recessed into the central portion 42.

The recessed central portion 42 has a depth in relation to the outermost portion of the first inner side 14 of the core which corresponds approximately to the thickness of the cover 28 such that the cover can be fully recessed into the central portion 42 so that the outer side of the cover 28 is substantially flush with the first side 14 of the core and the flange portion 40 of the resilient skin 18 which overlaps the perimeter portion 44 at the inner side 14 of the core.

The surface of the core at the central portion 42 thereof includes a resilient bonding layer 50 applied thereto formed of a silicone type material which is arranged to remain somewhat tacky or sticky in a finished cured state after application to the core. The resilient bonding layer 50 within the central portion 42 of the core 12 is arranged for mating with a similar resilient bonding layer 52 at the inner side of the cover 28.

The cover 28 according to FIGS. 12 and 13 comprises a core layer of flexible resilient material, for example a layer of foam material of approximately ⅛ of an inch in thickness. In other embodiments, the cover may have greater thickness for accommodating greater variations in a profile of a user to which the cover is to be mated. The resilient bonding layer 52 spans the full inner side of the core 54 of the cover while an additional resilient bonding layer 56 fully spans the opposing outer side of the core 54. Each of the resilient bonding layers 52 and 56 similarly comprise a silicone type material which remains somewhat adhesive to the touch in a cured state thereof. In this manner the bonding layer 52 at the inner side is suitable for forming a temporary adhesive bond to the bonding layer in the central portion of the core while the bonding layer 56 at the outer side of the cover is suitable for forming a temporary adhesive bond to the skin of the user which is sufficient to prevent relative sliding of the prosthesis against the skin of the user while remaining readily separable therefrom as may be desired.

Typically a plurality of covers 28 are provided which are substantially identical with one another so as to be interchangeably mounted within the recessed central portion 42 of the core for ease of cleaning by the user.

In some embodiments, the core together with the outer layers of resilient skin 18 may be formed as a standard element which is mass produced while the cover 28 at the inner side can be customized to have varying profile and thickness to accommodate different users. In this instance, the benefits of both mass production and custom fitting can be realized at the same time.

Since various modifications can be made in my invention as herein above described, and many apparently widely different embodiments of same made within the spirit and scope of the claims without department from such spirit and scope, it is intended that all matter contained in the accompanying specification shall be interpreted as illustrative only and not in a limiting sense.

The invention claimed is:

1. A method of forming a breast prosthesis comprising:
 providing a core formed of low density foam material;
 shaping a first side of the core to be substantially dome shaped so as to be substantially in a form of a breast;
 shaping a second side of the core opposite the first side to mate with a wearer of the prosthesis by trimming the foam material of the core;
 applying a plurality of outer layers of resilient skin in an uncured form to the first side of the core subsequently to shaping the first side of the core; and
 curing the resilient skin such that the resilient skin retains shape in a cured form.

2. The method according to claim 1 including forming the resilient skin to comprise silicone.

3. The method according to claim 1 including applying the outer layers such that the outer layers have a thickness which is less than 20% of an overall thickness of the prosthesis at a central location thereof.

4. The method according to claim 1 including shaping the second side of the core after the outer layers are applied to the first side.

5. The method according to claim 1 including applying the plurality of outer layers of resilient skin to the first side of the core such that at least an outermost one of the outer layers is substantially translucent.

6. The method according to claim 1 including applying color between at least some of the outer layers of resilient skin to define at least one of veins, an areola, or a tattoo.

7. The method according to claim 1 including adhering a nipple protrusion to the outer layers such that the nipple protrusion can be readily detached and reattached to the outer layers at any one of a plurality of mounting locations thereon.

8. The method according to claim 7 including providing a representation of an areola on the outer layers of resilient skin and supporting the nipple protrusion to be readily separable from the outer layers and the representation of the areola thereon.

9. The method according to claim 1 including providing a cover of flexible material arranged to span a second side of the core opposite the first side, and supporting the cover on the core to span the second side such that the cover is readily separable from the core and the outer layer.

10. A method of forming a breast prosthesis comprising:
providing a core formed of low density foam material;
shaping a first side of the core to be substantially dome shaped so as to be substantially in a form of a breast;
applying an outer layer of resilient skin to the first side of the core;
providing a plurality of covers, each formed of a different flexible material and each being arranged to be supported on the core to span the second side of the core so as to be readily separable from the core such that the plurality of covers are interchangeable with one another.

11. The method according to claim 10 including forming a peripheral retaining edge about a perimeter of the second side of the core and retaining a perimeter edge of each cover in relation to the retaining edge about a full perimeter of the cover.

12. The method according to claim 11 including providing a recessed central portion in the second side of the core which is bound by the peripheral retaining edge and mounting each cover in the recessed central portion to be substantially flush with a peripheral edge of the outer layer of resilient skin at the second side of the core.

13. The method according to claim 10 including applying a resilient bonding layer to the second side of the core and to an inner side of at least one of the covers to retain the cover spanning the second side of the core.

14. The method according to claim 10 including applying a resilient bonding layer to an outer side of at least one of the covers to retain the cover against a user.

15. The method according to claim 10 including applying a plurality of outer layers of resilient skin in an uncured form to the first side of the core subsequently to shaping the first side of the core and curing the resilient skin such that the resilient skin retains shape in a cured form.

16. The method according to claim 10 including shaping a second side of the core opposite the first side to mate with a wearer of the prosthesis by trimming the foam material of the core.

17. A method of forming a breast prosthesis comprising:
providing a core formed of low density foam material;
shaping a first side of the core to be substantially dome shaped so as to be substantially in a form of a breast;
applying an outer layer of resilient skin to the first side of the core;
forming a top edge of the core and the outer layer of resilient skin thereon to be gradually reduced in thickness towards the peripheral edge thereof; and
providing a retainer flange along opposing bottom edge of the core which is arranged to be overlapped by a bra strap of a wearer of the prosthesis.

18. The method according to claim 17 including applying a plurality of outer layers of resilient skin in an uncured form to the first side of the core subsequently to shaping the first side of the core and curing the resilient skin such that the resilient skin retains shape in a cured form.

19. The method according to claim 17 including shaping a second side of the core opposite the first side to mate with a wearer of the prosthesis by trimming the foam material of the core.

* * * * *